United States Patent
Collin et al.

(10) Patent No.: US 7,297,673 B2
(45) Date of Patent: Nov. 20, 2007

(54) THICKENER FOR HIGH-PH AQUEOUS SYSTEMS

(75) Inventors: Jennifer Reichl Collin, Devon, PA (US); Fanwen Zeng, Belle Mead, NJ (US); Paul Francis David Reeve, Grasse (FR)

(73) Assignee: Rohm and Haas Company, Philadelphia, PA (US)

( * ) Notice: Subject to any disclaimer, the term of this patent is extended or adjusted under 35 U.S.C. 154(b) by 208 days.

(21) Appl. No.: 11/211,350

(22) Filed: Aug. 25, 2005

(65) Prior Publication Data

US 2006/0046952 A1    Mar. 2, 2006

(30) Foreign Application Priority Data

Aug. 25, 2004  (EP)  .................................. 04292090
Mar. 2, 2005   (EP)  .................................. 05290466

(51) Int. Cl.
  *C11D 3/37*  (2006.01)
  *A61K 8/72*  (2006.01)

(52) U.S. Cl. ...................... 510/475; 510/477; 510/488; 424/486; 424/487; 424/70.11; 424/70.16

(58) Field of Classification Search ................ 510/475, 510/477, 488; 424/486, 487, 70.11, 70.16
See application file for complete search history.

(56) References Cited

U.S. PATENT DOCUMENTS

| | | | |
|---|---|---|---|
| 4,384,096 A | 5/1983 | Sonnabend | |
| 4,421,902 A | 12/1983 | Chang et al. | |
| 4,429,097 A * | 1/1984 | Chang et al. | ................ 524/558 |
| 4,514,552 A | 4/1985 | Shay et al. | |
| 4,836,948 A | 6/1989 | Corring | |
| 4,867,896 A | 9/1989 | Elliott et al. | |
| 5,529,711 A | 6/1996 | Brodbeck et al. | |
| 6,635,702 B1 | 10/2003 | Schmucker-Castner et al. | |
| 2004/0063855 A1* | 4/2004 | Tepe | .......................... 524/789 |

* cited by examiner

*Primary Examiner*—Brian Mruk
(74) *Attorney, Agent, or Firm*—Kenneth Crimaldi

(57) ABSTRACT

An aqueous composition having a pH of at least 10, and comprising from 0.1% to 5% of at least one crosslinked copolymer comprising from 2.5% to 65% (meth)acrylic acid residues, from 10% to 80% $C_2$-$C_4$ alkyl (meth)acrylate residues, from 2% to 25% lipophilically modified (meth)acrylate residues and residues of a crosslinker that has no ester or amide functionality.

11 Claims, No Drawings

THICKENER FOR HIGH-PH AQUEOUS SYSTEMS

This patent application claims the foreign priority benefit of French Patent application serial number 04292090.0 filed on Aug. 25, 2004 and French Patent application serial number 05290466.1 filed on Mar. 2, 2005 under 37 CFR 1.55(a).

This invention relates to an aqueous system having a high pH and a rheology-modifying polymer.

Rheology modifiers are used in aqueous cleaning products, including for example, shampoo, to increase viscosity at low shear rates while maintaining flow properties of the product at higher shear rates. In addition, rheology modifiers can provide effective, heat-age stable suspensions of particulate material or beads dispersed in the aqueous phase. A variety of copolymer thickeners made from vinyl monomers have been used for this purpose. For example, U.S. Application Pub. No. 2004/0063855, discloses an acrylic emulsion polymer of methacrylic acid, an alkyl acrylate, acrylic acid and stearyloxypoly(ethyleneoxy)$_{20}$ethyl methacrylate. However, such thickeners are intended for use in consumer products having near-neutral pH values. In contrast, industrial cleaning compositions and some personal care products can have pH values of at least 10.

The problem addressed by the present invention is the need for a rheology-modifying polymer having good stability and favorable rheological properties at high pH.

STATEMENT OF INVENTION

The present invention provides an aqueous composition having a pH of at least 10, and comprising from 0.1% to 5% of at least one crosslinked copolymer comprising from 2.5% to 65% (meth)acrylic acid residues, from 10% to 80% $C_2$-$C_4$ alkyl (meth)acrylate residues, from 2% to 25% lipophilically modified (meth)acrylate residues and residues of a crosslinker that has no ester or amide functionality.

DETAILED DESCRIPTION

Percentages are weight percentages based on the entire composition, unless specified otherwise. As used herein the term "(meth)acrylic" refers to acrylic or methacrylic, and "(meth)acrylate" refers to acrylate or methacrylate. The term "acrylic polymers" refers to polymers of acrylic monomers, i.e., acrylic acid (AA), methacrylic acid (MAA) and their esters, and copolymers comprising at least 50% of acrylic monomers. Esters of AA and MAA include, but are not limited to, methyl methacrylate (MMA), ethyl methacrylate (EMA), butyl methacrylate (BMA), hydroxyethyl methacrylate (HEMA), methyl acrylate (MA), ethyl acrylate (EA), butyl acrylate (BA), ethylhexyl acrylate (EHA), and hydroxyethyl acrylate (HEA), as well as other alkyl esters of AA or MAA, including the lipophilically modified monomers described below. Preferably, acrylic polymers have at least 75% of monomer residues derived from (meth)acrylic acid or (meth)acrylate monomers, more preferably at least 90%, more preferably at least 95%, and most preferably at least 98%. The term "vinyl monomer" refers to a monomer suitable for addition polymerization and containing a single polymerizable carbon-carbon double bond.

The lipophilically-modified copolymer used according to the invention contains lipophilically-modified (meth)acrylate residues each of which may contain either one, or a plurality of, lipophilic groups. According to one embodiment, such groups are suitably in the same copolymer component as and attached to hydrophilic chains, such as for example polyoxyethylene chains. According to another embodiment, the copolymer may contain a vinyl group which may be used to copolymerize the polymer to other vinyl-containing entities to alter or improve the properties of the polymer. Alternatively other copolymerization systems may be used. The polymerizable group may be attached to the lipophilic group directly, or indirectly for example via one or more, for example up to 60, preferably up to 40, water-soluble linker groups, for example, —CH[R]CH$_2$O— or —CH[R]CH$_2$NH— groups wherein R is hydrogen or methyl. Alternatively, the polymerizable group may be attached to the lipophilic group by reaction of the hydrophilic, for example polyoxyethylene, component with a urethane compound containing unsaturation. The molecular weight of the lipophilic-modifying group or groups is preferably selected together with the number of such groups to give the required minimum lipophilic content in the copolymer, and preferably, for satisfactory performance in a wide range of systems.

The amount of lipophilically-modified component in the copolymers useful in the present invention preferably is at least 5%, more preferably at least 10%, and most preferably at least 16%; and preferably is no more than 20%.

The lipophihic-modifying groups themselves are preferably straight chain saturated alkyl groups, but may be aralkyl or alkyl carbocyclic groups such as alkylphenyl groups, having at least 6, and up to 30 carbon atoms although branched chain groups may be contemplated. It is understood that the alkyl groups may be either of synthetic or of natural origin and, in the latter case particularly, may contain a range of chain lengths. For example, naturally sourced stearic acid, even of commercially pure quality may contain only about 90% of stearic chains, up to about 7% of palmitic chains and a proportion of other chains and lower quality products may contain substantially less stearic acid. It is intended herein that reference to the chain length of such groups is to the predominant chain length which is present as more than 50%, preferably in more than 75%, of the chains.

It is an important subsidiary feature of the invention that the chain length of the lipophilic-modifying groups be minimized and the alkyl chain length, or predominant chain length, preferably is below 25, more preferably from 8 to 22, and most preferably from 10 to 18 carbon atoms. The hydrophilic component of the lipophilically-modified copolymer may suitably be a polyoxyethylene component preferably comprising at least one chain of at least 2, preferably at least 5, more preferably at least 10, and up to 60, preferably up to 40, more preferably up to 30 ethylene oxide units. Such components are usually produced in a mixture of chain lengths.

Preferably, the $C_2$-$C_4$ alkyl (meth)acrylate residues in the copolymer used in this invention are $C_2$-$C_3$ alkyl (meth)acrylate residues, and most preferably EA. Preferably, the amount of $C_2$-$C_4$ alkyl (meth)acrylate residues is at least 20%, more preferably at least 30%, more preferably at least 40% and most preferably at least 50%. Preferably, the amount of $C_2$-$C_4$ alkyl (meth)acrylate residues is no more than 70%, more preferably no more than 65%, and most preferably no more than 60%. Preferably, the amount of (meth)acrylic acid residues in the copolymer used in the present invention is at least 15%, more preferably at least 17.5%, more preferably at least 20%, and most preferably at least 25%. Preferably, the amount of (meth)acrylic acid residues is no more than 65%, more preferably no more than 50%, more preferably no more than 40%, and most preferably no more than 35%. (Meth)acrylic acid residues are introduced into the copolymer by inclusion of either (meth) acrylic acid, or a (meth)acrylic acid oligomer having a polymerizable vinyl group, in the monomer mixture used to produce the copolymer. Preferably, the copolymer contains residues derived from acrylic acid in an amount no more than 30%, more preferably no more than 27.5%, more preferably no more than 25%, and most preferably no more than 22%. Preferably, the copolymer contains residues derived from acrylic acid in an amount of at least 2.5%, more preferably at least 5%, more preferably at least 7.5%, more preferably at least 10%, and most preferably at least 15%.

Optionally, the copolymer also contains from 2% to 25%, preferably from 5% to 20%, of a hydrophilic comonomer, preferably one having hydroxyl, carboxylic acid or sulfonic acid functionality. Examples of hydrophilic comonomers include 2-hydroxyethyl (meth)acrylate (HEMA or HEA), itaconic acid and acrylamido-2-methylpropanesulfonic acid.

The aqueous compositions of the present invention contain from 0.5% to 5% of at least one copolymer; i.e., the total amount of copolymer(s) is in this range. Preferably, the amount of copolymer in the aqueous composition is at least 0.75%, more preferably at least 1%, and most preferably at least 1.25%. Preferably, the amount of copolymer in the aqueous composition is no more than 4%, more preferably no more than 3%, and most preferably no more than 2.5%. Preferably, the copolymer is an acrylic polymer. The copolymer, in aqueous dispersion or in the dry form, may be blended into an aqueous system to be thickened followed by a suitable addition of acidic or basic material if required.

Preferably, the pH of the aqueous composition is at least 10.5. In one embodiment of the invention, the pH is at least 11. Preferably, the pH is no more than 14, more preferably no more than 13. In one embodiment of the invention, the pH is no more than 12.

The aqueous compositions of the present invention preferably contain from 0.5% to 25% of at least one surfactant, i.e., the total amount of surfactant(s) is in this range. Preferably, the aqueous compositions of the present invention contain at least 1% of at least one surfactant. Preferably, the aqueous composition contains no more than 10%, more preferably no more than 4%, and most preferably no more than 2.5%, of at least one surfactant.

The surfactant(s) preferably is selected from the groups of anionic surfactants characterized by carboxylate, sulfonate, sulfate or phosphate solubilizing groups, and nonionic surfactants characterized by amide or hydroxyl groups or ethylene oxide chains. Cationic, amphoteric or zwitterionic surfactants may also or alternatively be used provided that they are compatible with the thickening copolymer and other ingredients of the aqueous system in the quantity required by the invention. Cationic surfactants characterized by amine or ammonium solubilizing groups, and/or amphoteric surfactants characterized by combinations of the anionic and cationic solubilizing groups may be selected. Preferred surfactants for use in the practice of the invention may be selected from the $C_8$ to $C_{18}$ fatty acids or their water soluble salts, water soluble sulfates of $C_8$ to $C_{18}$ alcohols, sulfonated alkylaryl compounds such as, for example, dodecylbenzene sulfonate, alkylphenoxy polyethoxy ethanols, for example with $C_7$ to $C_{18}$ alkyl groups and 9 to 40 or more oxyethylene units, ethylene oxide derivatives of long chain carboxylic acids, for example of lauric, myristic, palmitic or oleic acids, ethylene oxide derivatives of long chain alcohols, for example of lauryl or cetyl alcohols, alkanolamides and polyglucosides, for example the alkyl polyglucosides. Suitable cationic surfactants may be, for example, lauryl pyridinium chloride, octylbenzyltrimethyl-ammonium chloride, dodecyl trimethylammonium chloride and ethylene oxide condensates of primary fatty acid amines.

The composition of the present invention optionally may include other ingredients, e.g., salts, co-rheology modifiers (e.g. Laponite™ clay, cellulosics, carrageenan, xanthan, other acrylic or urethane rheology modifiers), organic or inorganic particles (including, for example, abrasives, beads, mica, encapsulated oil beads), dispersed liquids, dispersants, biocides, enzymes, bleach, emollient, fragrance, dyes, thioglycolic acid, etc.

The copolymer of the present invention is crosslinked, that is, a crosslinker, such as a monomer having two or more ethylenic unsaturated groups, is included with the copolymer components during polymerization. The crosslinker does not have ester or amide functionality. Preferred examples of such monomers include divinylbenzene, trimethylolpropane diallyl ether, tetraallyl pentaerythritol, triallyl pentaerythritol, diallyl pentaerythritol and allyl sucroses. Divinylbenzene, trimethylolpropane diallyl ether (TMPDE) and tetraallyl pentaerythritol are especially preferred. The amount of crosslinker residue in the polymer is typically at least 0.01%, preferably at least 0.1%, based on weight of the copolymer components. Preferably, the amount of crosslinker residue in the polymer is no more than 2.5%, more preferably no more than 2.2%. In one embodiment of the invention in which the crosslinker is difunctional, e.g., divinylbenzene, preferably the amount of crosslinker residue in the polymer is at least 0.5%, more preferably at least 1%, and most preferably at least 1.5%. In another embodiment of the invention in which the crosslinking agent is more than difunctional, preferably the amount of crosslinker residue in the polymer is no more than 1.0%, more preferably no more than 0.5%. Additional residues of other crosslinkers which contain ester or amide groups may be present.

In one embodiment of the invention, the copolymer is prepared in the presence of a chain transfer agent when a crosslinking agent is used. Examples of suitable chain transfer agents are carbon tetrachloride, bromoform, bromotrichloromethane, and compounds having a mercapto group, including 3-mercaptopropionic acid or long chain alkyl mercaptans and thioesters such as dodecyl-, octyl-, tetradecyl- or hexadecyl-mercaptans or butyl-, isooctyl- or dodecyl-thioglycolates. When used, the amount of chain transfer agent is typically from 0.01% to 5%, preferably from 0.1% to 1%, based on weight of the copolymer components. If the crosslinking agent is used in conjunction with a chain transfer agent, which are conflicting operations for polymerization purposes, not only is exceptional efficiency observed but also very high compatibility with hydrophilic surfactants, as manifested by increased product clarity.

The rheology modifier may be prepared by copolymerizing the monomers using known aqueous or inverse emulsification procedures at an acidic pH, inverse emulsion polymerization at neutral pH, or precipitation or solution polymerization processes. In such processes, any other suitable additives known in the art, for example, a free-radical initiator such as peroxygen or diazo compounds and, optionally, chain transfer agents may be used. Suitable peroxygen compounds may be peroxides, hydroperoxides, persulfates or organic peroxides and a suitable quantity of initiator may be 0.01% to 3% by weight of the components of the copolymer. The copolymerization temperature is typically 25° C. to 92° C., more preferably 60° C. to 90° C. The copolymer emulsion may be recovered by filtration and the copolymer may, if desired, be provided in dry form by spray drying or coagulation. U.S. Pat. Nos. 4,384,096, 4,663,385, 4,429,097 and 4,514,552 may be consulted for further general and specific details of suitable copolymerization and recovery techniques, and of suitable monomers and additives. The molecular weight of uncrosslinked lipophilically modified copolymer is typically in the range of about 100,000 to 1 million.

A particular aqueous composition in which the copolymer is useful is a hard surface cleaner. Typical components of a hard surface cleaner, in addition to the copolymer thickener and surfactant mentioned previously, include sufficient base to attain a pH of 10-13, and optional ingredients, including 0.25-5% electrolyte, 1-10% glycol, and 0.5-5% silicate salts, e.g., potassium or sodium silicate or metasilicate. Typically, the surfactant used is either a nonionic or anionic surfactant, or a mixture of both. The copolymer may also be used in abrasive hard surface cleaner, which contains 5-35% calcium carbonate in addition to the ingredients listed above.

Another aqueous composition in which the copolymer is useful is a depilatory. Typical components of a depilatory include the copolymer, thioglycolic acid or its salts, alkali to achieve a pH of 11-13, and optional ingredients, including calcium hydroxide, glycerin, nonionic and/or anionic surfactant, mineral oil, fatty alcohol, and sodium silicate. (See *Chemistry and Manufacture of Cosmetics*, $3^{rd}$ Edition, Vol. 2, Ch. 11; Allured Publishing Corp., Carol Stream Ill., 2000).

The copolymer also is useful in cream hair relaxer formulations. Other ingredients of these formulations include 1-10% glycol, 5-20% petrolatum, base to achieve pH of 10.5-13, and optional ingredients, including 0.5-10% guanidine, 0.5-10% nonionic surfactant, 1-10% mineral oil, 1-15% fatty alcohol and 0.2-2% cationic polymer. (See *Chemistry and Manufacture of Cosmetics*, $3^{rd}$ Edition, Vol. 2, Ch. 17,19; Allured Publishing Corp., Carol Stream Ill., 2000).

Other formulations in which the copolymer is useful include hair gel (alcohol-containing and alcohol-free); hair styling cream, paste, or gum; shampoo, conditioner, 2 in 1 conditioning shampoo, body wash/shower gel, liquid soap, sunscreen lotions and sprays, tanning lotions, skin care lotions, two-part hair dyes, permanent waving formulations, textile and hard surface cleaners, e.g., laundry detergent, liquid auto-dish detergent, manual dish detergent, spot-pretreaters, oven cleaners, and glass/window cleaners, and thickening all types of alcohol or water/alcohol formulations. The copolymer may also be used as a polymeric emulsifier with or without co-emulsifiers or surfactants.

EXAMPLE

Preparation of Test Samples:
1. Weigh 50 g of Hard Surface Cleaner Base[1] into a small beaker.
2. Weigh out sufficient copolymer to have 2.0% copolymer in final formulation. Predilute rheology modifier with 5.0 g of deionized water.
3. Add diluted polymer to beaker with stirring. Mix until fully incorporated.
4. Adjust pH of formulation to 11 with 10% NaOH solution.
5. q.s. to 60 g total with deionized water. Allow sample to equilibrate for >1 h and adjust pH if necessary with NaOH or citric acid.
6. Split sample. To one portion, add 0.1 g of polyethylene beads and mix to incorporate. Second portion will be used for rheology measurements.
7. Measure rheology of sample[2] after one day at room temperature and after heat aging at 45° C. or 60° C. Monitor bead suspension at room temperature, 45° C., 60° C.

[1] Hard Surface Cleaner Base contains 2-3.5% of a blend of anionic and nonionic surfactants and 2-3% of salts, with a pH of approximately 11.
[2] Rheology analysis conducted on a TA Instruments AR 2000 rheometer at 25° C. with a 60 mm 0.5° steel cone. A standard steady state flow from low to high shear stress method was used for analysis, with shear stress ramp from 0.002 Pa to 700 Pa.

| \multicolumn{2}{c}{List of Polymers} |  |
|---|---|
| Entry | Copolymer composition |
| Polymer 1 | 18 Lipo1[a]/52EA/10MAA/20AA//0.2DAP/0.1n-DDM |
| Polymer 2 | 18 Lipo1/52EA/10MAA/20AA//1.6DVB/0.1n-DDM |
| Polymer 3 | 18 Lipo1/52EA/10MAA/20AA//2.0DVB/0.1n-DDM |
| Polymer 4 | 18 Lipo1/52EA/10MAA/20AA//1.8 DVB/0.1n-DDM |
| Polymer 5 | 18 Lipo1/52EA/10MAA/20AA//0.135 triallyl isocyanurate/0.1n-DDM |
| Polymer 6 | 18 Lipo1/52EA/10MAA/20AA//0.15 Methylene-bisacrylamide/0.1n-DDM |
| Polymer 7 | 18 Lipo1/52EA/10MAA/20AA//0.12Tetraallyl Pentaerythritol/0.1n-DDM |
| Polymer 8 | 18 Lipo1/52EA/10MAA/20AA//0.116Trimethylolpropane Diallyl ether/0.1n-DDM |
| Polymer 9 | 3 Lipo3[b]/15Lipo1/52EA/10MAA/20AA/ 0.116TMPDE/0.1n-DDM |
| Polymer 10 | 6 Lipo3/12 Lipo1/52EA/10MAA/20AA/ 0.116TMPDE/0.1n-DDM |
| Polymer 11 | 9 Lipo3/9 Lipo1/52EA/10MAA/20AA/ 0.116TMPDE/0.1n-DDM |
| Polymer 12 | 18 Lipo1/52EA/10MAA/20AA//0.08Tetraallyl Pentaerythritol/0.1n-DDM |

[a] Lipo1 is a lipophilically modified monomer having a linear saturated $C_{16-18}$alkyl group connected through about 18–26 oxyethylene residue to a methacryloyl group.
[b] Lipo3 is a lipophilically modified monomer having a linear saturated $C_{20-24}$alkyl group connected through 20–28 oxyethylene residues to a methacryloyl group.
c. DAP is diallyl phthalate.
d. nDDM is n-dodecyl mercaptan.
e. TMPDE: trimethylolpropane diallyl ether Polymer 1 contains residues of a diallyl phthalate (DAP) crosslinker, which contain ester groups, so that Polymer 1 is not within the scope of the claimed invention and is included for comparative purposes only. Similarly, Polymer 6 contains residues of a methylene-bisacrylamide crosslinker, which contain amide groups, so that Polymer 6 also is not within the scope of the claimed invention and is included for comparative purposes only.

| Sample | Temp/Duration | Viscosity (Pa · s) at Shear Rate of $1e^{-4}$/s | Viscosity (Pa · s) at Shear Rate of 1/s |
|---|---|---|---|
| \multicolumn{4}{c}{2.0% Polymer 2 vs. 2.0% Polymer 1 at pH 11, 45° C.} |
| 2.0% Polymer 2 | Initial | 685 | 5 |
| 2.0% Polymer 2 | 45° C./4 weeks | 2077 | 9 |
| 2.0% Polymer 1 | Initial | 1316 | 11 |
| 2.0% Polymer 1 | 45° C./4 weeks | 69 | 16 |
| \multicolumn{4}{c}{2.0% Polymer 5 at pH 11, 45° C.} |
| 2.0% Polymer 5 | Initial | 875 | 15 |
| 2.0% Polymer 5 | 45° C./1 week | 552 | 18 |
| 2.0% Polymer 5 | 45° C./2 weeks | 579 | 19 |

-continued

| Sample | Temp/Duration | Viscosity (Pa · s) at Shear Rate of 1e⁻⁴/s | Viscosity (Pa · s) at Shear Rate of 1/s |
|---|---|---|---|
| 2.0% Polymer 5 | 45° C./3 weeks | 507 | 18 |
| 2.0% Polymer 5 | 45° C./4 weeks | 374 | 19 |
| 2.0% Polymer 2 vs. 2.0% Polymer 3 vs. Polymer 4 at pH 11, 60° C. | | | |
| 2.0% Polymer 2 | Initial | 642 | 5 |
| 2.0% Polymer 2 | 60° C./10 days | 1386 | 10 |
| 2.0% Polymer 3 | Initial | 633 | 5 |
| 2.0% Polymer 3 | 60° C./10 days | 3085 | 11 |
| 2.0% Polymer 4 | Initial | 531 | 5 |
| 2.0% Polymer 4 | 60° C./10 days | 1278 | 10 |
| 2.0% Polymer 7 at pH 11, 60° C. | | | |
| 2.0% Polymer 7 | Initial | 560 | 10 |
| 2.0% Polymer 7 | 60° C./7 days | 569 | 12 |
| 2.0% Polymer 7 | 60° C./10 days | 435 | 13 |
| 2.0% Polymer 8 at pH 11, 60° C. | | | |
| 2.0% Polymer 8 | Initial | 1199 | 12 |
| 2.0% Polymer 8 | 60° C./7 days | 1889 | 17 |
| 2.0% Polymer 8 | 60° C./10 days | 1442 | 16 |
| 2.0% Polymer 6 at pH 11, 25° C. vs. 45° C. | | | |
| 2.0% Polymer 6 | Initial | 177 | 14 |
| 2.0% Polymer 6 | 25° C./1 week | 208 | 18 |
| 2.0% Polymer 6 | 25° C./2 weeks | 175 | 17 |
| 2.0% Polymer 6 | 25° C./3 weeks | 155 | 19 |
| 2.0% Polymer 6 | 25° C./4 weeks | 150 | 20 |
| 2.0% Polymer 6 | 45° C./1 week | 174 | 18 |
| 2.0% Polymer 6 | 45° C./2 weeks | 142 | 17 |
| 2.0% Polymer 6 | 45° C./3 weeks | 111 | 18 |
| 2.0% Polymer 6 | 45° C./4 weeks | 49 | 18 |

The data in the Tables above demonstrate that Polymers 2-5 and 7-8, which are within the scope of the present invention, provide pH-stable high viscosities at low shear rates, and low viscosities at high shear rates. In contrast, Polymer 1, which has ester functionality in its crosslinker residues, and Polymer 6, which has amide functionality in its crosslinker residues, do not provide high viscosity at low shear rate after aging in a high-pH formulation.

The invention claimed is:

1. An aqueous composition having a pH of at least 10, and comprising from 0.1% to 5% of at least one crosslinked copolymer comprising from 2.5% to 65% (meth)acrylic acid residues, from 10% to 80% $C_2$-$C_4$ alkyl (meth)acrylate residues, from 2% to 25% lipophilically modified (meth)acrylate residues and residues of a crosslinker selected from among the group consisting of trimethylolpropane diallyl ether, tetraallyl pentaerythritol, triallyl pentaerythritol, diallyl pentaerythritol and allyl sucroses.

2. The composition of claim 1, further comprising from 0.5 to 25% of at least one surfactant.

3. The composition of claim 2 in which the crosslinker is at least one of trimethylolpropane diallyl ether and tetraallyl pentaerythritol.

4. The composition of claim 3 in which the pH is no more than 13.

5. The composition of claim 4 in which said at least one copolymer has from 5% to 25% acrylic acid residues.

6. The composition of claim 5 containing from 0.75 to 4% of said at least one copolymer.

7. The composition of claim 6 in which said at least one copolymer further comprises methacrylic acid residues, and the acrylic acid plus the methacrylic acid residues total from 20% to 40% of the copolymer.

8. The composition of claim 7 in which the residues of crosslinker are present in the copolymer in an amount from 0.1% to 2.5%.

9. The composition of claim 8 in which said at least one copolymer contains from 16% to 20% lipophilically modified (meth)acrylate residues.

10. The composition of claim 9 in which said at least one surfactant is present in an amount from 1% to 5%.

11. The composition of claim 10 in which said (meth)acrylic acid residues consist essentially of methacrylic acid residues and 15% to 22% acrylic acid residues, and the acrylic acid plus methacrylic acid residues total from 20% to 40%; said residues of crosslinker are present from 0.1% to 0.5%; and said $C_2$-$C_4$ alkyl (meth)acrylate residues consist essentially of 40% to 60% ethyl acrylate residues; all as percentages of said copolymer.

* * * * *